(12) United States Patent
Wollmann et al.

(10) Patent No.: US 6,449,036 B1
(45) Date of Patent: Sep. 10, 2002

(54) SENSOR UNIT, PROCESS AND DEVICE FOR INSPECTING THE SURFACE OF AN OBJECT

(75) Inventors: Christian Wollmann, Liegau; Lutz Wenert, Weissig; Joachim Ihlefeld; Ralf Grieser, both of Dresden, all of (DE)

(73) Assignee: Baumer Optronic GmbH, Radeberg (DE)

(*) Notice: Subject to any disclaimer, the term of this patent is extended or adjusted under 35 U.S.C. 154(b) by 0 days.

(21) Appl. No.: 09/403,735
(22) PCT Filed: Apr. 23, 1998
(86) PCT No.: PCT/IB98/00614
§ 371 (c)(1),
(2), (4) Date: Jan. 10, 2000
(87) PCT Pub. No.: WO98/49545
PCT Pub. Date: Nov. 5, 1998

(30) Foreign Application Priority Data

Apr. 25, 1997 (DE) .......................................... 197 17 488

(51) Int. Cl.⁷ ............................................... G01N 21/00
(52) U.S. Cl. .................... 356/237.2; 356/601; 356/629; 356/237.1; 359/216; 359/219; 359/211
(58) Field of Search ........................... 356/237.1–237.5, 356/238.1–238.3, 338–340, 600, 601, 607, 608, 629; 250/234–236, 406.1–406.2, 216, 458.1; 359/212, 211, 216–219; 351/205

(56) References Cited

U.S. PATENT DOCUMENTS

| | | | |
|---|---|---|---|
| 3,976,384 A | | 8/1976 | Matthews et al. |
| 4,176,907 A | * | 12/1979 | Matsumoto et al. ......... 359/217 |
| 4,286,880 A | | 9/1981 | Young |
| 4,744,663 A | * | 5/1988 | Hamashima et al. ..... 356/237.5 |
| 5,177,511 A | * | 1/1993 | Feuerstein et al. .......... 351/205 |
| 5,712,719 A | * | 1/1998 | Hama ......................... 250/236 |
| 5,838,001 A | * | 11/1998 | Minakuchi et al. ......... 250/236 |
| 5,847,400 A | * | 12/1998 | Kain et al. ............... 250/458.1 |
| 5,953,120 A | * | 9/1999 | Hencken et al. ............ 356/338 |

FOREIGN PATENT DOCUMENTS

| | | |
|---|---|---|
| EP | 387 521 A2 | 9/1990 |
| EP | 408 920 A2 | 1/1991 |

(List continued on next page.)

OTHER PUBLICATIONS

Patent Abstracts of Japan, Publication No: 59040149, Pulbication Date: May 3, 1984, Apparatus For Detecting Live Knot.
Patent Abstracts of Japan, Publication No. 60019117, Publication Date Jan. 31, 1985.

(List continued on next page.)

Primary Examiner—Frank G. Font
Assistant Examiner—Sang H. Nguyen
(74) Attorney, Agent, or Firm—Rankin, Hill, Porter & Clark LLP

(57) ABSTRACT

A sensor unit (50), a device, and a process for inspection of a surface (10', 10Δ) of an object (10) for the purpose of identifying surface characteristics, such as structural defects. The device contains an emitting module (51) and a receiving module (52). The emitting module emits at least one beam bundle (6, 6', 6"). The receiving module has at least one light receiver (15, 16, 20). A rotating polygonal mirror wheel (2) is located in the focal point of a parabolic mirror (1). A beam bundle (6) of the laser (3, 4) is directed onto the mirror (1) by means of a telecentric lens, which guides the emitter and receiver beam on the same optical axis, whereby the parabolic mirror (1) guides the deflected beam bundle (6, 6', 6") under a constant angle relative to the axis of symmetry (7) of the parabolic mirror (1) along a scanning line (23, 24) over the object (10). The diffusely reflected beam bundle, after being deflected out of the common beam path, impinges on the processing unit (5).

25 Claims, 6 Drawing Sheets

FOREIGN PATENT DOCUMENTS

| | | |
|---|---|---|
| EP | 0 198 037 B1 | 3/1991 |
| EP | 701 116 A1 | 3/1996 |
| EP | 786 643 A2 | 7/1997 |
| JP | 06281873 * | 10/1994 |

OTHER PUBLICATIONS

Patent Abstracts of Japan, Publication No. 59040149, Publication Date Mar. 5, 1984.
WO 95/24636.
WO 93/11403.

* cited by examiner

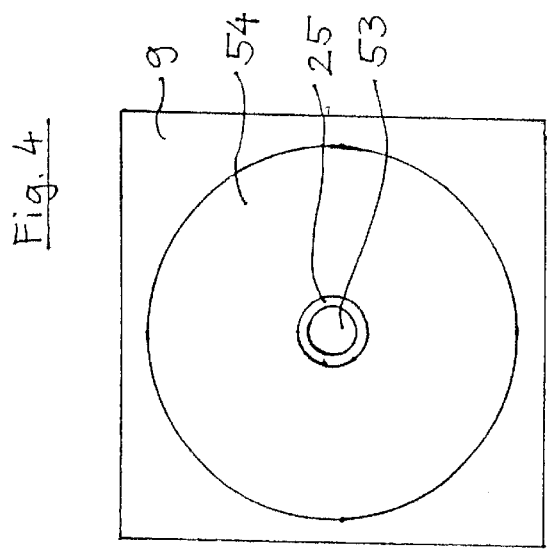
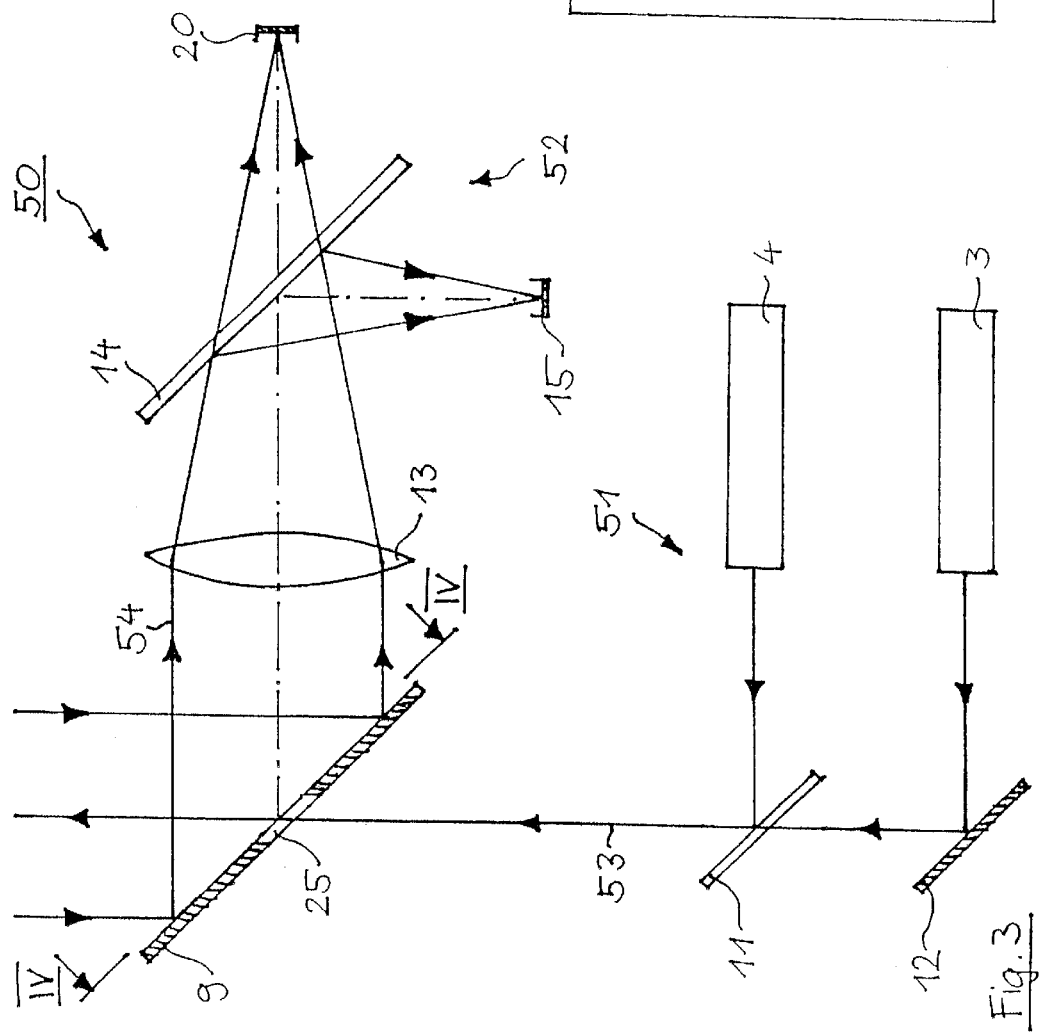

SENSOR UNIT, PROCESS AND DEVICE FOR INSPECTING THE SURFACE OF AN OBJECT

BACKGROUND OF THE INVENTION

The invention concerns a device and a process for the inspection of the surface of an object.

With respect to the surface inspection of materials, it is known to scan the respective surface with charge-coupled device (CCD), line, or matrix cameras as well as with laser scanners. It is also known in the art to analyze the gray-scale value or color pictures with image processing means.

In the case of the processing of wood, for example in door and window manufacture, or in the fabrication of veneer sheets, it is necessary to investigate and determine the quality of the wood to be processed. In doing so, it should be determined whether the wood has shakes, fissures, knot holes, protrusions or indentations. It should also be determined whether the wood has blue stain or red ring rot, which makes them unsuitable for the foreseen purpose.

Prior to the present invention, wood surfaces have normally been manually inspected. It is up to now practically impossible to automatically identify wood which is affected by blue stain or red ring rot. There are a number of technical problems, which generally are associated with the great depth of focus and the simultaneously high resolution called for by the process as well as with the transportation speed of the wood. For this, relatively elaborate illumination equipment with a very high performance is necessary.

When illuminating wood by means of a laser beam, the so-called scatter effect occurs, which means that a part of the light is dispersed into the wood fibers. The light scatters in the vicinity of the surface in a function of the local density distribution. In the case of an undisturbed fiber orientation, a characteristic dipole distribution in the spatial intensity distribution of the diffusely reflected light is manifest, whereby the (1/e) drop, the integral intensity, as well as the actual structure of the maxima of the emissions are dependent on the type of material and on the structure of the defect. Through SE-A-7500465-5, a process and a device utilizing a helium-neon laser has become known, where the scatter effect is indirectly exploited for the evaluation.

Through EP-0 198 037 B1, a process for measuring the fiber angles in a fibrous material, such as wood, has become known. In the EP '037 process, an area on the surface of the material is illuminated with an impinging ray of light and photo-sensitive devices are spatially arranged in such that they measure the light reflected by the illuminated area. The fiber angle is measured relative to three reference axes perpendicular to one another (x, y, z) and any point on the surface of the material is defined as the point of origin of the axes. The illuminated area encompasses the point of origin and has a diameter, which is at least ten times the size of the average fiber diameter of the substance to be measured. A majority of the photo-sensitive devices are positioned so as to be able to assess the azimuthal angular positions around the point of origin of the intensity maximum of the reflected light. Furthermore, a number of arbitrary points in transverse and longitudinal direction of an area on the surface of the material are staked out, in order to be in a position to assess the azimuthal angular positions of the intensity maxima at each of the points. By means of the relationship between the azimuthal angular position of the reflected light maxima and the fiber angle, for every measuring point the corresponding fiber angle is calculated relative to all three axes in order to indicate the complete pattern of the fiber angles within the measured area of the fibrous material. For carrying out this process, a highly elaborate installation is necessary in order to, on the one hand, measure the radiated beam proportion of the reflected light and, on the other hand, measure the proportion of the diffusely reflected light.

DE-A-196 04 076.0 proposes a device for the inspection of the surface of wood for the purpose of determining surface characteristics. The DE '076 device includes an opto-electronic sensor, an electronic and/or optical processing unit, a computer capable of real-time operation. With the De '076 device, the wood can be moved relative to the sensor, as well as an incremental position transducer, which synchronizes the sensor with the speed of the wood. The sensor consists of a color laser scanner with at least two beam bundles of differing wave lengths and a receiver with two channels with one opto-electrical receiving element each. The channels are formed by beam splitting of the reflected beam bundle. A lens for creating an intermediate image plane is located in at least one of the channels. After the lens, within one of the channels there is an optical graduated filter, which is capable of modulating the passing light current to the opto-electrical receiving element belonging to it independent of the position. The signals of the receiving element of the channel without the graduated filter are converted into a color image in the computer. The signals of the other channel, the light current of which has been modulated independent of the position, are converted into a profile image of the surface.

It is, for example, known from U.S. Pat. No. 4,286,880 and JP 59 040 149 A that wood surfaces can be investigated by scanning with a light beam. These two documents divulge a rotating mirror, which is located in the focal point of a parabolic mirror. Light is emitted onto the rotating mirror from a light source and from there distributed by reflection on the parabolic mirror along a scanning line on the wood surface. In U.S. Pat. No. 4,286,880, the subject is an improvement of work stations for the localization of wood defects, wherein an operating person has to find the defects. The operating person marks the defects and the marks are detected by an optical sensor with a binary output signal. The object of JP 59 040 149 A is the detection of live knots by means of asymmetrically scattered light. For the solution of this problem, a wood surface is scanned by a light beam and light scattered from the wood surface is directly detected by two detectors arranged symmetrically with respect to the scanning beam.

From the state of the technology, optical distance sensors are also known. The distance sensor divulged in EP-0 387 521 A2 is based on a triangulation process. A beam of light is focused on the surface to be measured by means of a lens. Light scattered by the surface is collected by the same lens and focused on position-sensitive detectors by a concave mirror. The components are positioned relative to an optical axis such that a high light sensitivity is assured by a small angle of incidence. Another distance sensor, divulged in WO 93/11403, contains a rotating polygonal mirror, which distributes light emitted from a light source onto a scanning line on the surface to be measured. A scanning lens projects the point-shaped light source onto the surface. The light reflected by the surface is projected onto a point-shaped detector by means of the same scanning lens and a further lens. A maximum light intensity impinges on the detector only when the object is in the focal plane of the scanning lens and when the detector is simultaneously in the focal plane of the further lens. The detected light intensity is therefore a measure for the distance of the object from the scanning lens. The construction can be refined by utilizing several detectors, each of which supply maximum signals at differing object distances.

SUMMARY OF THE INVENTION

The present invention is directed toward a device and a process for the dynamic inspection of the surfaces of objects such as wood, tile, textile, and glass. The present invention is further directed toward a device and process for the identification of surface characteristics. With the present invention an automatic inspection of the surface can be carried out continuously and with a high speed. The continuous, high speed inspection provided by the present invention permits characteristics such as shakes, fissures, cracks, knot holes, protrusions, indentations, and, in the case of wood, blue stain or red ring rot, to be identified with certainty by the exploitation of the scatter effect. In particular, simultaneously the position-dependent diffuse reflection of a surface, the distance of the surface as well as the deviation of the diffuse reflection characteristic as a function of the position can be detected by a Lambert projector at processing speeds of several meters per second in real time. Apart from this, the device shall be of a simple construction and should be able to be manufactured at a low cost.

In accordance with the present invention, a device for inspecting a surface of an object for the purpose of identifying surface characteristics contains a sensor unit and a lens. The device also has a scanning device, to which light is transmitted from the sensor unit. The scanning device comprises a concave mirror, in the focal point of which is located a light deflecting element that is illuminated by the sensor unit and having with a deflection angle dependent on time. Accordingly, the light transmitted by the sensor unit can be guided over the object along a scanning line and light from the scanning device diffusely reflected by the object impinges on the sensor unit.

In further accordance with the present invention, the device includes a parabolic mirror, in the focal point of which a rotating polygonal mirror is located, onto which the beam bundle of the laser is directed by means of a telecentric lens, which guides the transmitter and receiver beam along the same optical axis. The parabolic mirror guides the deflected beam bundle over the object along a scanning line under a constant angle relative to the symmetry axis of the parabolic mirror, and guides the beam bundle diffusely reflected by the object back along the same path. The beam bundle, after being reflected out of the common beam path, impinges on the processing unit.

The device is based on the fact of the so-called Tracheid effect (scatter effect) which occurs with density changes on the surface in the case of a number of materials with a point-shaped, coherent illumination. In doing so, light enters into the material through the surface and is guided inside the material. The guidance of the light within the material and its damping are determined by the structure of the material. The device and the process exploit the scatter effect for the evaluation of surface anomalies and carry out an assessment of surface defects under real time conditions.

In the beam path between the laser and the polygonal mirror wheel there is a mirror with an aperture or hole, through which the irradiated beam bundle passes and impinges on the polygonal mirror wheel. The mirror deflects the diffusely reflected beam bundle onto a lens at a given angle. Optical detectors and the electronic processing unit, in preference including a computer capable of real time operation, are situated in the focal plane of the lens. After the lens and in front of its focal plane, two beam bundles and preferably at least two channels are created by beam splitting, which are evaluated separately. A high precision of execution is important for the functioning of the device.

If, for example, the material to be inspected is wood, then around the intensive light spot of the direct irradiation two light cones are formed, aligned to the direction of the fibers. The light cones diminish corresponding to the dipole characteristic and join the direct light spot of the impinging beam. In correspondence with the change of the surface structure and the direction of the fibers, the two light cones change with respect to their length, brightness and direction. The brightness, length and direction are dependent on the local defect and its shape as well as on the direction of the fibers. The inventors have discovered that, through the scatter effect, for the first time in the case of wood just starting blue stain or red ring rot can be made visible, long before the attack can be identified by the unaided eye, chemical analyses or microscopic viewing. Equally on the basis of the scatter effect defects in the wood, such as, for example, knot holes, compression, red or blue stain become visible, which lead to a diminution of the quality of the corresponding wood.

In order to obtain a surface profile (3D - profile) by means of a triangulation process, at least one light beam emitted from the sensor unit can be guided onto the object. Light diffusely reflected from the object under a finite angle relative to the impinging beam can be guided back to the sensor unit in such a manner that the impinging and the returned light beam are essentially in coincidence in a plane parallel to the surface of the object. In an alternative version, plural laser beams can be guidable by means of various mirrors that are offset relative to one another such that the individual laser beams are in coincidence in the horizontal plane, while in the vertical object plane a constant angle is given, in order to measure the surface profile by means of the vertical deposition of the diffusely reflected laser light with a position-sensitive opto-electrical receiving element, which is in particular a PSD sensor element capable of high speed.

In further accordance with the present invention, at least one laser beam is focused on the surface of the object in order to obtain a 3D surface profile by triangulation. The vertical deposit of the diffusely reflected laser light is measured through an additional guidable mirror under a constant angle by means of a position-sensitive receiving element (PSD) capable of high speed.

A process for the inspection of the surface of an object to identify surface characteristics in accordance with the present invention utilizes a sensor unit that emits light to a scanning device, and wherein the object is moved relative to the sensor unit. The emitted light is focused on the object by means of a telecentric projection and guided over the object along a scanning line under a constant angle relative to the object to be scanned, and relative to the vertical line of the transportation surface. Light diffusely reflected by the object is guided back to the sensor unit along the same beam path as the emitted light.

In accordance with another embodiment of the inventive process, the laser beam is focused on the object by means of a telecentric projection, which guides the emitted and received beam along the same optical axis, focuses it on the object, and guides it along a scanning line always under a constant angle relative to the object to be scanned, and relative to the vertical line of the transportation surface of the object. This can be the most effectively achieved by the arrangement of a parabolic mirror, in the focal point of which a polygonal mirror wheel is located, so that the angle of the laser beam is constant with respect to the symmetry axis of the parabolic mirror. The spatial resolution is limited solely by the focusing ability of the laser light. The telecentric beam bundle of the moving laser light spot, the measuring point, along a scanning line, does not have to impinge orthogonally on the surface to be scanned, the angle of impingement can rather be any one within wide ranges. The angle must, however, be constant relative to the normal line of the transportation surface of the object. In doing so, the diffusely reflected light is guided back to the detector through the same projection system.

In further accordance with the process, various surface characteristics can be measured in real time, namely:

a) the intensity distribution of the diffusely reflected laser light, and/or b) the distribution of the intensity of the laser light scattered by local density variations (Tracheid effect), which is observed through spatial filters in the scatter channel, and/or c) the elevation profile (3D channel) of the surface, which is measured by means of a triangulation process, and/or d) double refraction characteristics, which are measured by means of detection processes dependent on polarization, for example by means of an analyzer parallel and anti-parallel to the surface direction.

After the lens, and in front of the image plane of the lens, at least two channels are formed by beam splitting into two partial beam bundles, which are assessed. On principle, it is even possible to detect all characteristics mentioned above with only one laser, which can be implemented by a modification of the receiving module. For splitting the diffusely reflected laser radiation into partial radiation bundles according to their differing wave lengths, a dichroic mirror is positioned in the beam path. From the partial beam bundles of differing wave lengths various surface characteristics, such as the elevation profile in the 3D channel, the reflectivity in a red light channel as well as the Tracheid effect in the mentioned scatter channel are simultaneously recorded with a high repetition rate. One of the partial radiation bundles formed by the dichroic mirror, preferably the red light proportion of the diffusely reflected laser beams, is again split into two channels by means of a semi-transparent mirror, in which in accordance with the diffusely reflected laser light sensitive sensors are located. Within one channel the image of the directly diffusely reflected light point or spot on the object is evaluated and the image of the light cones of the scatter effect is blanked out and from the image of the laser point or spot a gray-scale image is obtained. Inside the other channel (scatter channel) by means of special spatial filters the directly diffusely reflected light point or spot is blanked out and only the image of the remaining light cones is evaluated. Blanking out is accomplished by means of special spatial filters.

The Tracheid—scattered laser light (scatter channel), which, for example, in the case of wood serves for the evaluation of the image of the remaining light cones, is detected in a real time process for making visible density-dependent surface anomalies, such as shakes, cracks, fissures, structural defects. The density-dependent surface anomalies are detected by means of a four-quadrant process, for example by means of dichroic mirrors or a four-quadrant diode, position dependent in the form $(S_x+S_y)/S$ and in the direction arctan $(S_x/S_y)$, if necessary in combination with the triangulation process in the 3D channel also in function of the elevation, the spatial resolution of which is only limited by the focusing ability of the laser light.

BRIEF DESCRIPTION OF THE DRAWINGS

These and further features of the present invention will be apparent with reference to the following detailed description and drawings, wherein:

FIG. 3 is a schematic cross section of a third embodiment of the sensor unit in accordance with the invention;

FIG. 4 is a top view of a deflecting element of the sensor unit of FIG. 3;

DETAILED DESCRIPTION OF THE PREFERRED EMBODIMENTS

Figure 1:
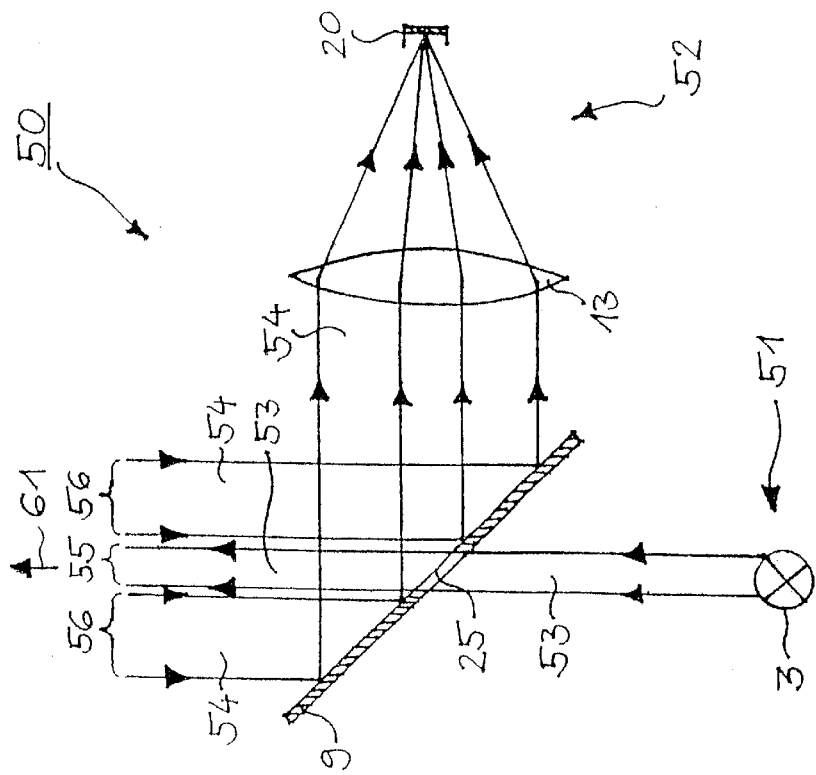
FIG. 1 is a schematic cross section of a first embodiment of the sensor unit in accordance with the invention.

FIG. 1 shows a schematic cross section through the first embodiment of the sensor unit 50 in accordance with the invention. The sensor unit 50 serves to emit light to a scanning device 60 (FIGS. 5–6, not illustrated in FIG. 1), which is situated in the direction of an arrow 61, and for receiving light impinging from the scanning device 60. The sensor unit 50 contains a light-emitting sender module 51 and a light receiving receiver module 52. The emitting module 51 contains at least one light source 3, which can be a laser, a light-emitting diode (LED) or another light source. In front of the light source 3, if necessary, there can be a focusing optical system (not illustrated). The receiving module 52 contains at least one light receiver 20, such as a photo-diode, a CCD camera, a position-sensitive receiving element (PSD), etc. An optical system 13, such as a focusing lens or a multi-element lens, can project an object (not illustrated in FIG. 1) onto the light receiver 20.

The sensor unit 50 also has an optical deflection element 9. If light from the direction of the scanning device 60 impinges on the sensor unit 50, the light is split-up by the deflecting element 9 into first and second light beam paths 53, 54, which differ from one another. The first beam path 53 is defined by a first spatially limited part 55 of the light. The second beam path 54 is defined by a second spatially limited part of the light 56. The first beam path 53 has a smaller cross sectional area than the second beam path 54. The emitting module 51 is located in the first beam path 53 and the receiving module 52 is located in the second beam path 54. In this embodiment the deflection element 9 is designed as a plane mirror with an aperture 25 and arranged such that light traveling to the deflection element 9 is, to a greater extent, left to pass through to the scanning device 60 through the aperture 25. Light emanating from the scanning device 60 outside the first beam path 53 is, in contrast, to a greater extent reflected to the receiving module 52. The surface shell, which surrounds the aperture 25 in the deflection element 9, is in preference parallel to the direction of diffusion of the emitted light 53.

Figure 2:
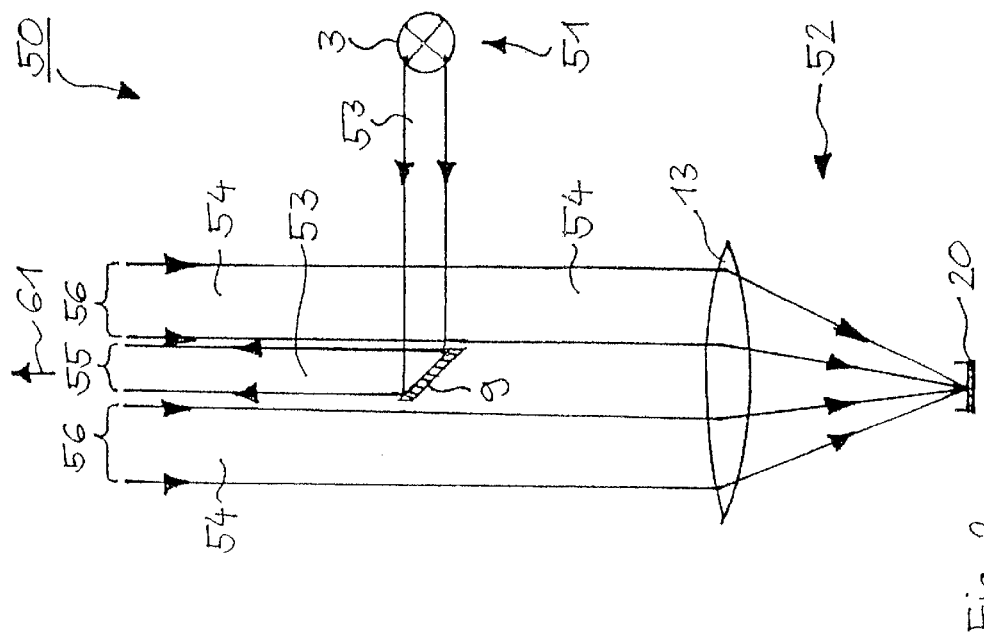
FIG. 2 is a schematic cross section of a second embodiment of the sensor unit in accordance with the invention.

In FIG. 2, a second preferred embodiment of the sensor unit in accordance with the invention 50 is schematically illustrated. Here the deflection element 9 is designed as a small mirror and arranged such that light 53 traveling from the emitter module 51 to the deflection element 9 is, to a greater extent, reflected to the scanning device 60 (not illustrated in FIG. 2). Light 54 emanating from the scanning device outside the first beam path 53 is, in contrast, to a greater extent allowed to pass through to the receiving module 52.

FIG. 3 schematically illustrates a further preferred embodiment of the sensor unit in accordance with the invention 50. The deflection element 9 corresponds to that of FIG. 1. This embodiment contains two light sources 3, 4, for example, two lasers. A first laser 3 emits red light in the wave length range between about 620 nm and 770 nm, preferably 680 nm. A second laser 4 emits infrared light in the wave length range above 770 nm, preferably 830 nm. The two laser beams are joined by means of a mirror 12 and a beam splitter 11.

The receiving module 52 contains two light receivers 15, 20 and a beam splitter 14. Light 54 impinging on the receiving module 52 is split-up by the beam splitter 14 and delivered to the light receivers 15, 20. The beam splitter 14 can have dichroic characteristics. In other words, the reflection to transmission ratio of the splitter 14 can be dependent on the wave length.

FIG. 4 schematically illustrates a top view of the mirror 9 with aperture 25 of FIG. 3 along the line IV—IV. Light 54 emanating from the scanning device 60, which exactly coincides with the light 53 traveling to the scanning device 60, does not impinge on the receiving module 52. Rather, the portion of light emanating from the scanning device 60 that coincides with the light 53 traveling to the scanning device 60 will pass through the aperture 25. This way a "cross-talk" is efficiently prevented.

Figure 5:
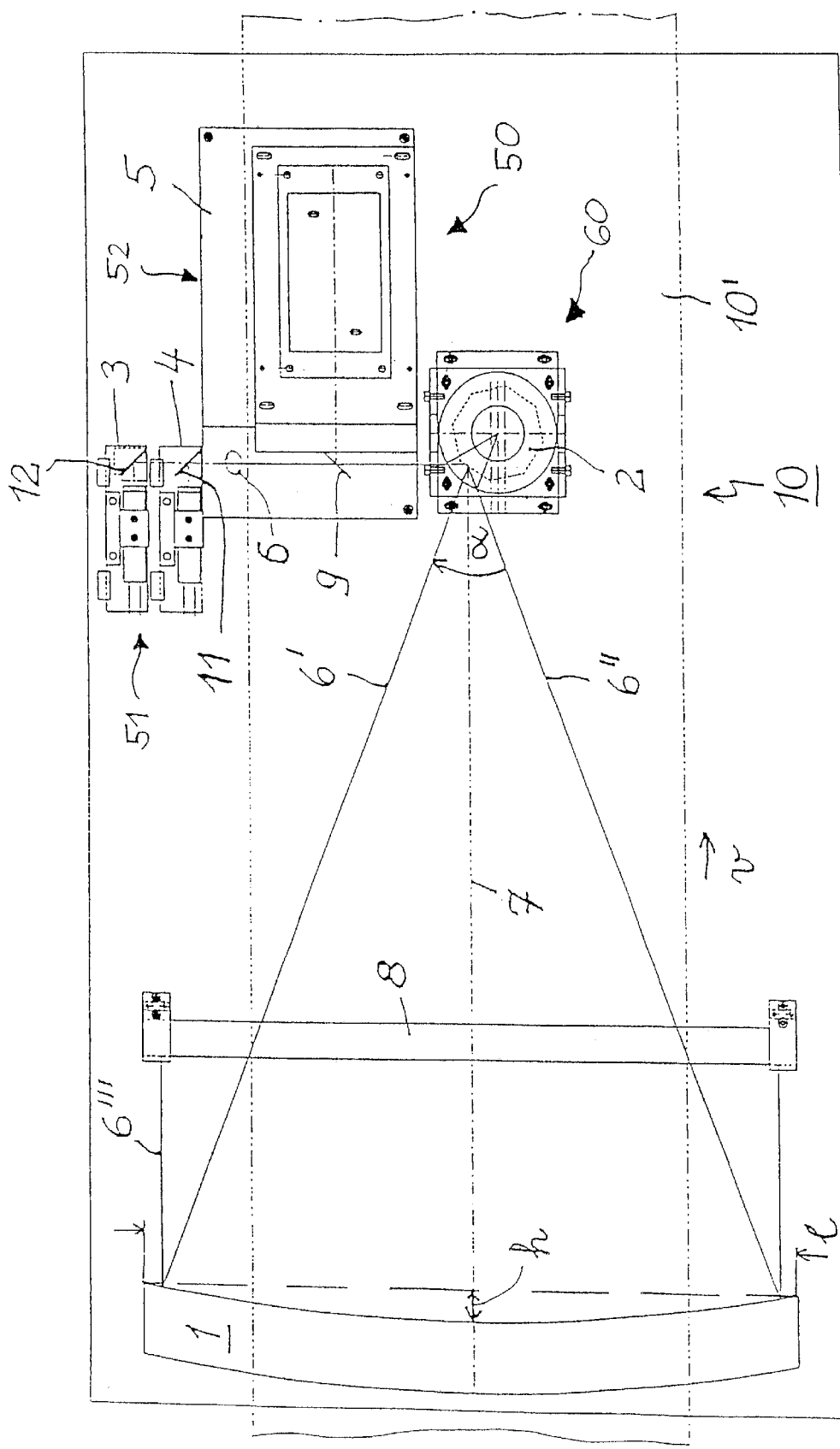
FIG. 5 is a schematic layout of the device in accordance with the invention in top view.

In accordance with FIG. 5, the fundamental principle of the device in accordance with the invention consists of a concave mirror 1, which is preferably cut out of a paraboloid as a narrow strip having length 1 and height h. Preferred as a concave mirror is a parabolic mirror, because it provides an ideal, practically aberration-free image. Within the focal point of the parabolic mirror 1 is a polygonal mirror wheel 2, which is rotated by a motor at a high speed, with one of its polygon surfaces arranged in such a manner, that preferably at an angle of 45 degrees to the normal line of the polygon surface of the mirror wheel to the optical axis 7 (symmetry axis) of the parabolic mirror 1, the center of the polygon surface comes to lie exactly in the focal point of the parabolic mirror 1.

Two lasers 3, 4 each generate a laser beam. One laser preferably operates in the wave length range of approximately 680 nm, therefore in the red light range. The other laser preferably operates in the wave length range of 830 nm, therefore in the infrared light range. The laser beams are deflected by mirrors 11, 12 and brought together into a common beam 6. For this purpose, the mirror 11 illustrated in FIG. 1 is transparent for the laser beam of the laser 3 situated behind it.

The combined laser beams 6 pass through a hole 25 in a further mirror 9 and impinge on one of the plane polygon surfaces of the rotating polygonal mirror wheel 2. Dependent on the design of the polygonal mirror wheel 2 and on the center distance of it from the parabolic mirror 1, the polygonal mirror wheel 2 guides the laser beams 6, 6', 6" at a certain predefined horizontal image field angle α over the parabolic mirror 1 in its longitudinal expanse 1, as can be seen in FIG. 5.

The horizontal image field angle a is limited by the laser beams 6', 6". The laser beam 6''' is reflected by the parabolic mirror 1 and guided parallel to itself over the longitudinal expanse of the parabolic mirror 1 and forms the scanning line. The reflected laser beam 6''' is guided to an inclined mirror and impinges on the surface 10' of an object to be scanned, for example a piece of wood traveling with the speed v relative to the laser. In this manner, the laser beams 6 from the lasers 3, 4, which are focused on the object 10, are guided under a constant angle relative to the symmetry axis 7 of the parabolic mirror 1, i.e., to the normal line of the transportation surface of the object 10, to the object 10 to be scanned, along the scanning line 23, 24 (i.e., FIG. 7). The object surface 10' is projected onto the light receiver contained in the receiving module as a telecentric image.

As discussed hereinbefore with respect to FIGS. 1–4, the laser light diffusely reflected in the point of impingement is guided back along the same path, so that the arriving beam and the diffusely reflected beam in essence coincide. The polygonal mirror wheel 2 projects the diffusely reflected beam bundle onto the mirror 9, which deflects the reflected beam bundle and guides it to a processing unit 5. The processing unit 5, which evaluates the diffusely reflected beam bundle optically and electrically, comprises a computer capable of real time operation.

Figure 6:
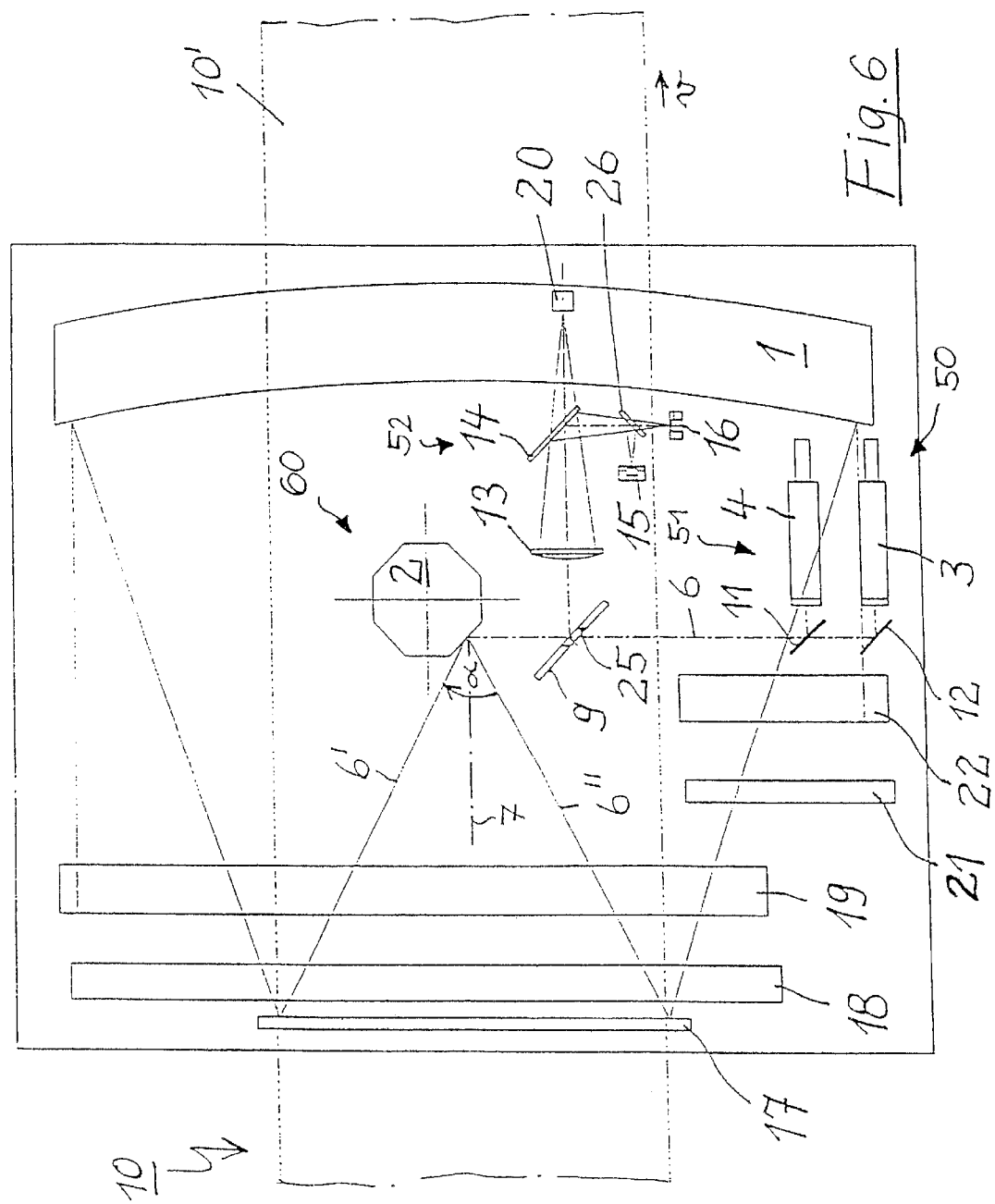
FIG. 6 is a top view of a technical embodiment of the device in accordance with the invention, in which the beam path is folded in order to achieve a small depth of the construction.
Figure 7:
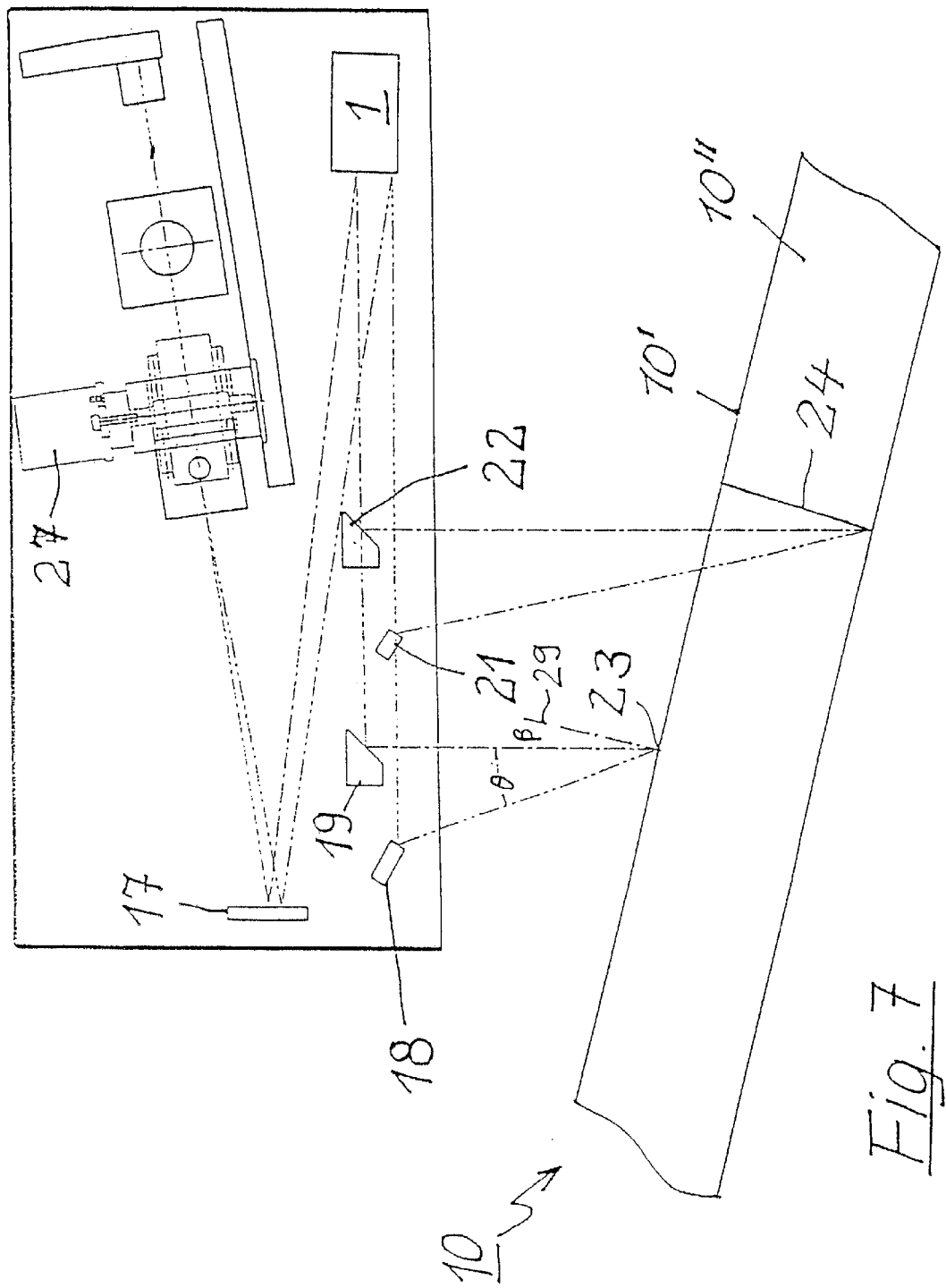
FIG. 7 is a side view of the device of FIG. 6.

In the FIGS. 6 and 7, a technical embodiment of the device is illustrated. The two lasers 3, 4 generate laser beams 6, which are brought together by mirrors 11, 12. The laser beams 6 are projected onto the rotating polygonal mirror wheel driven by a motor 27, rotating at high speed, through a hole 25 within the mirror 9. The mirror 9 is located in the focal point range—this time relative to a longish, plane mirror 17—of the parabolic mirror 1. The two laser beams 6 are projected onto the mirror 17 by the polygonal mirror wheel 2, which reflects the laser beams onto the parabolic mirror 1, so that the folded beam path illustrated in FIGS. 6 and 7 is produced.

The parabolic mirror 1 now has the effect that the laser beams reflected by it can be guided parallel to one another onto the surface 10'. The reflected beams, therefore, are at a constant angle relative to its symmetry axis 7, relative to a normal line 29 of the transportation surface 10' of the object 10.

To do this, in the beam path after the parabolic mirror 1, as shown in FIG. 7, there are two plane mirrors 18, 19. The plane mirrors 18, 19 are aligned transverse to the surface 10' of the object 10 to be scanned and guide the laser beams traveling parallel in one another along a scanning line 23 over the surface 10'. Two mirrors 18, 19 are used in order to, with respect to the evaluation in the triangulation process, obtain a 3D depiction of the image. If the information in the direction of the vertical axis is not required, then only one mirror 19 is necessary for the construction of the device and for carrying out the process.

In the following, with reference to FIG. 7, beam paths for the case without triangulation process and for the case with triangulation process are discussed. The light beam emitted by the sensor unit 50 and reflected by the parabolic mirror 1 impinges on the object 10 through mirror 19. The angle of impingement β of the light 10' relative to the normal line 29 is greater than zero. In other words, the light is not perpendicular to the surface 10'. As a consequence, light directly reflected from the surface 10' does not travel back to the mirror 19, but rather travels away from the mirror. Therefore, diffuse reflection on the surface 10' is measured.

In the case without triangulation process, light is measured, which returns to the sensor unit 50 under the same angle of reflection β through the mirror 19 on the same path as the impinging light. If a triangulation process is to be utilized, then the vertical deposition of light is measured, which is diffusely reflected under a constant angle θ relative to the impinging light and returns to the sensor unit 50 through a further mirror 18. Also in this case, the light in essence travels along the same path back to the sensor unit 50 as the impinging light. In this case, the angle θ determines the resolution of the 3D measurement. The greater the angle θ, the more sensitively the 3D profile can be measured. A preferred value for the angle θ is θ=15.50°±1.5°. In an alternative version of the process, light can be beamed onto the object 19 both through mirror 19 as well as through mirror 18—or even on more than two light paths, and the respective diffusely reflected light portions detected.

Two further mirrors 21, 22, which in the top view are arranged laterally from the mirrors 18, 19 and, if necessary, in different planes, serve to simultaneously guide the laser beams over a side surface 10" of the object 10 and along a further scanning line 24. Accordingly, a further image is obtained, also as a 3D image, so that simultaneously two planes 10', 10" inclined relative to one another at a given angle can be scanned. In the illustrated example the surfaces are inclined 90 degrees to one another. The diffusely reflected light beams travel back along the same path (i.e.—via parabolic mirror 1 and mirror wheel 2) and impinge on the mirror 9 under the horizontal image field angle α, from where they are deflected towards a lens 13.

With respect to FIG. 6, a dichroic mirror 14 is located in the beam path of the lens 13. The dichroic mirror 14 is transparent to infrared radiation of the diffusely reflected laser light, but deflects the diffusely reflected red light radiation of the other laser. After the mirror 14, in the image field plane of the lens 13 there is a receiver 20, the received signals of which are utilized as 3D information. With this information, a relief image can be calculated in the computer, which enables the identification of depth changes of the object to be inspected. A position-sensitive, opto-electrical receiving element, in particular a PSD sensor element capable of high speed, is preferably used as a sensor element 20 for the 3D channel. The PSD sensor element detects the positional deviation of the laser beam relative to the zero position, which has been guided through the mirror 18, 21.

Figure 8:
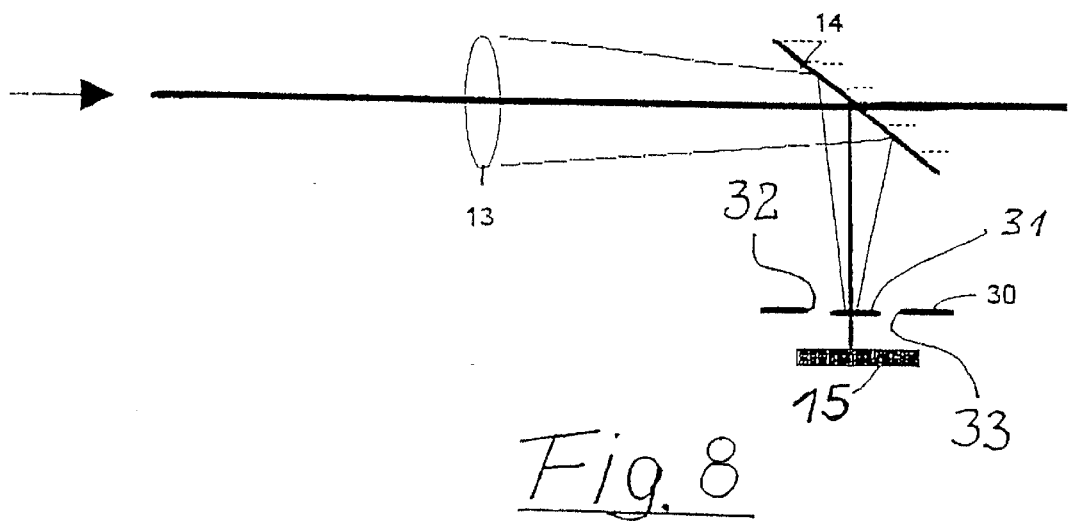
FIG. 8 is a view of a receiving module with a spatial filter vertical to the parabolic mirror in the scatter channel; and, FIG. 9 is a view of the receiving module of FIG. 8 with the same spatial filter parallel to the parabolic mirror in the scatter channel.
Figure 9:
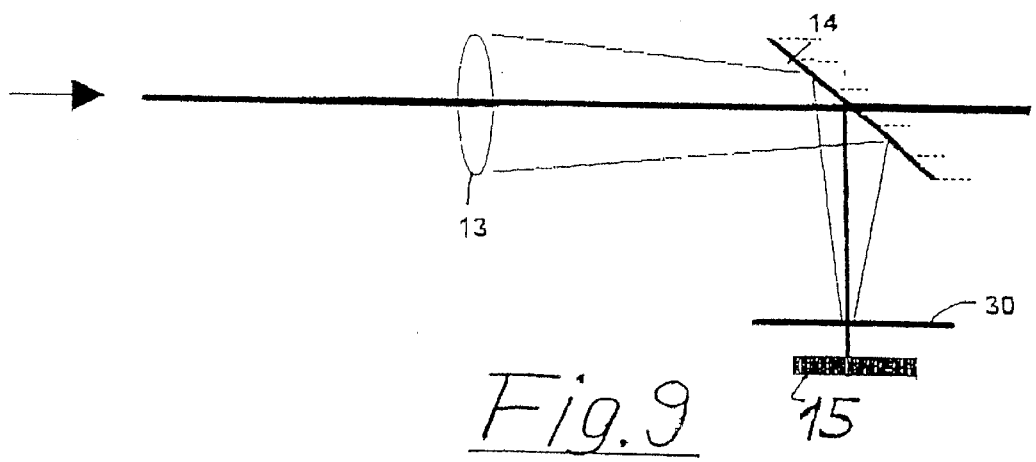

The red light portion of the diffusely reflected laser beams is deflected through the dichroic mirror 14 and impinges onto a splitter mirror 26. The splitter mirror 26 splits-up the red light portion into two channels in which light-sensitive sensors 15, 16 are located. One channel is operated as a so-called direct red sensor and provides a gray-scale image, wherein the image of the direct light point or spot on the object is evaluated. For this purpose, by means of a diaphragm the light cones of the scatter effect are blanked out. The other channel is the so-called scatter channel and serves to evaluate the actual scatter image and, thus, in the case of wood, the light cones, which adjoin the direct light spot. To do this, the center point or center spot, which is, of course, evaluated in the other channel, is blanked out be means of special spatial filters 30 in the scatter channel (FIGS. 8–9). The image of the remaining light cones, for example, is projected on to a four-quadrant diode. The position of the cones relative to one another and relative to the direction of transport can be calculated from the relationship of the two light cones to one another. Therefore, in the case of wood, for example, the fiber direction or places affected with blue stain or red ring rot can be identified. The evaluation of the diffusely reflected laser radiation is, therefore, carried out such that the energetic and/or the positional distribution of the diffusely reflected radiation is converted into different electrical signals.

By means of a computer capable of real time operation, the channels can be subsequently evaluated and the images generated displayed on a monitor. It is equally possible to convert the signals from the three channels into color values, in order to thus also generate a color image.

It is also conceivable to transmit the diffusely reflected laser radiation to a CCD camera for evaluation. FIGS. 8 and 9, on one hand, show a view of the receiving module 15 with a spatial filter 30 vertical to the parabolic mirror 1 in the scatter channel with lens 13 and mirror 14. On the other hand, FIGS. 8 and 9 show a view of the same receiving module 15 with the same spatial filter 30 parallel to the parabolic mirror in the scatter channel. One can make out the spatial blanking-out of the center spot by a central plate 31, whereby the light cones impinge on the light receiver 15 through slits 32, 33.

The device and the process are, in particular, suitable for assessing the surface of an object, especially surfaces of flat objects such as woods, tiles, textiles, glasses, plastic surfaces, foils, silicon wafers, cardboard and others. The device and process of the present invention is useful for identifying surface characteristics or defects such as shakes, fissures, cracks, holes, protrusions and indentations, and to evaluate such surfaces according to quality criteria. The device and process of the present invention are, in particular, suitable for inspection of woods, because they permit, for the first time, direct evaluation of the scatter effect in the case of wood and provide a selective optical contrast enhancement, in the case of the most diverse surface defects, or enable a differentiation of woods with saw roughness. Equally, blue stain as well as dirt contamination or damage resulting from worms or cracks/shakes are made very well visible. The usefulness of the invention consists in particular of the fact, that with it in real time various surface characteristics can be measured, such as:

a) the intensity distribution of the diffusely reflected laser light, and/or b) the distribution of the intensity of the laser light scattered by local density variations (Tracheid effect), which is observed through spatial filters in the scatter channel, and/or c) the elevation profile (3D channel) of the surface, which is measured by means of a triangulation process, and/or d) double refraction characteristics, which are measured by detection processes dependent on polarization, for example by means of an analyzer parallel and anti-parallel to the surface direction.

What is claimed is:

1. A device for inspecting a surface of an object to determine surface characteristics of the object, said device comprising:

a scanning device, and an optical sensor unit comprising:

a sending module for emitting light to the scanning device, a receiving module for receiving light incident from the scanning device, and an optical deflecting element that is operable to split light incident from the scanning device into a first beam path and a second beam path, said first beam path being different than said second beam path, said first beam path being defined by a first spatially limited part of the incident light and said second beam path being defined by a second spatially limited part of the incident light, and where the first spatially limited part has a cross sectional area that is smaller than a cross sectional area of the second spatially limited part, wherein the scanning device includes:

a light deflecting element, said light deflecting element having a time-dependent deflection angle, and a concave mirror having a focal point and an axis of symmetry (7), wherein said light deflecting element is located in said focal point so that light emitted from the sensor unit can be guided into the sensor unit under a constant angle relative to the symmetry axis of the concave mirror along a scanning line over the object and so that light diffusely scattered from the object emanating from the scanning device can be guided into the sensor unit along a path identical to the emitted light and wherein the concave mirror is disposed relative to the object surface and the receiving module such that the surface can be telecentrically projected into the receiving module and the light deflecting element acts as an aperture diaphragm, said receiving module further comprising at least one light receiver with a special filter or a diaphragm designed and positioned in a manner that directly diffusely scattered light is blanked out for said at least one light receiver, in order to detect tracheid scattered light.

2. The device according to claim 1, wherein the deflecting element is a mirror with an aperture and is positioned such that a major portion of light traveling from the emitting module to the deflecting element passes through the aperture to the scanning unit.

3. The device according to claim 1, wherein the deflecting element is a mirror and is positioned such that a major portion of light traveling from the sending module to the deflecting element is reflected to the scanning device by the mirror.

4. The device according to claim 1, wherein the emitting module includes a plurality of light sources that produce light having different wave lengths.

5. The device according to claim 4, wherein said plurality of light sources includes at least a first light source and a second light source, said first light source emits light having a wave length between about 620 nm and 770 nm, and said second light source emits light having a wave length above 770 nm.

6. The device according to claim 1, wherein the receiving module includes an optical system, the optical system being positioned between said deflecting element and said at least one light receiver such that the at least one light receiver is disposed in the focal plane of the optical system.

7. The device according to claim 6, wherein the receiving module includes several light receivers and at least one beam splitter, whereby by means of said at least one beam splitter, light impinging on the receiving module can be split up among the light receivers.

8. The device according to claim 7, wherein the at least one beam splitter has a wave length dependent reflection to transmission ratio.

9. The device according to claim 7, wherein a further spatial filter or diaphragm is positioned ahead of a light receiver for blanking out light cones from a scatter effect.

10. The device according to claim 1, including two light receivers, each of said two light receivers having a spatial filter or diaphragm arranged in a manner that directly diffusely scattered light is blanked out, said spatial filters being positioned orthogonally relative to one another to measure directional dependence of tracheid scattered light.

11. The device according to claim 1, wherein the receiving module includes at least one CCD camera or at least one position-sensitive receiving element.

12. The device according to claim 1, wherein the light deflecting element is a rotating polygonal mirror wheel.

13. The device according to claim 1, wherein the concave mirror is a strip having parallel cut edges out of a paraboloid.

14. The device according to claim 1, wherein, for obtaining a 3D profile by a triangulation process, at least one light beam emitted from the sensor unit can be guided on to the object and light diffusely scattered from the object under a constant angle ($\theta$) relative to the incident beam can be guided back to the sensor unit such that the incident beam and the guided back beam are coincident in a plane parallel to the surface of the object.

15. The device according to claim 14, wherein, for obtaining a telecentric 3D profile by means of a triangulation process, the sensor unit includes a position-sensitive receiving element capable of high speed, in order to measure the surface profile by deposition of the diffusely scattered light vertically to the object surface by means of telecentric projection.

16. The device according to claim 1, wherein the object is movable relative to the sensor unit.

17. A process for inspecting a surface of an object to determine surface characteristics thereof, wherein light emitted from a sensor unit is transmitted to a scanning device and the emitted light is guided to and deflected by a deflecting element wherein the light deflected by the deflecting element is focused on the object by a concave mirror having a focal point and a symmetry axis, the light deflecting element being positioned at said focal point, said deflected light being guided under a constant angle relative to the symmetry axis of the concave mirror along a scanning line over the object, and light diffusely reflected from the object is generally guided back to the sensor unit along the same path as the emitted light, wherein the object surface is telecentrically projected into the sensor unit by the concave mirror, whereby the light deflecting element acts as an aperture diaphragm and wherein additionally the intensity of tracheid scattered light guided back to the sensor unit is measured by a receiver, the directly diffusely scatted light being blanked out for the receiver.

18. The process according to claim 17, wherein the tracheid scattered light is measured by two receivers, each of said two receivers comprising a spatial filter for blanking out the directly diffusely scattered light point, the spatial filters being positioned orthogonally relative to one another to measure directional dependence of tracheid scattered light.

19. The process according to claim 17, wherein for obtaining a 3D profile by a triangulation process, at least one light beam emitted by the sensor unit is guided on to the object and light directly diffusely scattered from the object under a constant angle ($\theta$) relative to the incident beam is guided back to the sensor unit such that the incident beam and the guided back beam are coincident in a plane parallel to the surface of the object.

20. The process according to claim 17, wherein various surface characteristics are measured in real time using parallel processors.

21. The process according to claim 17, further comprising separating light portions of differing wave length impinging on the sensor unit from one another, and instantaneously recording, from the light portions, with a high repetition rate, various surface characteristics, said surface characteristics including elevation profile in a 3D channel, reflectivity in a red light channel, and tracheid effect in a scatter channel (15).

22. The process according to claim 21, comprising splitting up light impinging on the sensor unit into first and second light portions, and guiding the first and second light portions to two light receivers, said first light portion having the image of the light cones of the scatter effect blanked out, the image of the directly diffusely reflected light point on the object is evaluated and from grey-scale image is obtained, and in the case of the second light portion, the directly diffusely reflected light point is blanked out by special spatial filters and only the image of the remaining light cones is evaluated by said receiver.

23. The process according to claim 22, comprising the further steps of separating light portions of differing wave length impinging on the sensor unit from one another, whereby, with a first light portion in a triangulation process, 3D information is measured by means of a position sensitive receiving element and, with a second light portion, the intensity distribution of the object as well as the surface characteristics are measured with opto-electrical sensor elements.

24. The process according to claim 17, wherein light impinging on the sensor unit makes density-dependent surface anomalies visible and, by means of a four-quadrant process, which is a function of the position $(S_x+S_y)$ and the direction arctan $(S_x+S_y)$ and, if necessary. in combination with the triangulation process in a 3D channel, which is a function of the elevation, is detected in a real time process, the spatial resolution of which is limited only by a focusing ability of the light.

25. The process according to claim 17, further comprising moving the object relative to the sensor unit.

* * * * *

UNITED STATES PATENT AND TRADEMARK OFFICE
CERTIFICATE OF CORRECTION

PATENT NO. : 6,449,036 B1
DATED : September 10, 2002
INVENTOR(S) : Wollmann et al.

It is certified that error appears in the above-identified patent and that said Letters Patent is hereby corrected as shown below:

<u>Title page,</u>
Item [57], ABSTRACT,
Line 2, delete "(10', 10Δ)" and insert -- (10', 10") --.

<u>Column 8,</u>
Line 3, delete "a" and insert -- α --.
Line 8, after "object" insert -- 10 --.

<u>Column 11,</u>
Line 57, after "whereby" insert -- , -- (comma).

<u>Column 14,</u>
Line 11, delete "$(S_x + S_y)$" and insert -- $(S_x + S_y)/S$ --.

Signed and Sealed this

Thirty-first Day of December, 2002

JAMES E. ROGAN
*Director of the United States Patent and Trademark Office*